US008871869B2

(12) United States Patent
Dias et al.

(10) Patent No.: US 8,871,869 B2
(45) Date of Patent: *Oct. 28, 2014

(54) HYDROPHILIC COATING

(75) Inventors: Aylvin Jorge Angelo Athanasius Dias, Maastricht (NL); Guido Joseph Elisabeth Hensen, Oirsbeek (NL); Johannes Wilhelmus Belt, Geleen (NL); Marnix Rooijmans, Born (NL); Nicolaes Hubertus Maria de Bont, Stein (NL); Edwin Peter Kennedy Currie, Sittard (NL)

(73) Assignee: DSM IP Assets B.V., Heerlen (NL)

( * ) Notice: Subject to any disclaimer, the term of this patent is extended or adjusted under 35 U.S.C. 154(b) by 1075 days.

This patent is subject to a terminal disclaimer.

(21) Appl. No.: 12/096,096

(22) PCT Filed: Dec. 11, 2006

(86) PCT No.: PCT/EP2006/011903
§ 371 (c)(1),
(2), (4) Date: Jun. 4, 2008

(87) PCT Pub. No.: WO2007/065721
PCT Pub. Date: Jun. 14, 2007

(65) Prior Publication Data
US 2008/0292776 A1    Nov. 27, 2008

(30) Foreign Application Priority Data

Dec. 9, 2005 (EP) .................................... 05111906
Jun. 1, 2006 (EP) .................................... 06011433
Sep. 13, 2006 (EP) .................................... 06019147

(51) Int. Cl.
*C08L 33/24* (2006.01)
*A61L 33/00* (2006.01)
*B05D 3/00* (2006.01)
*A61L 29/08* (2006.01)
*C08J 7/04* (2006.01)
*C09D 5/00* (2006.01)

(52) U.S. Cl.
CPC ............... *A61L 29/085* (2013.01); *C08J 7/047* (2013.01); *C09D 5/00* (2013.01)
USPC .......................................... 525/218; 427/2.1

(58) Field of Classification Search
USPC ............... 427/2, 2.31, 2.1, 2.3, 2.25; 525/218
See application file for complete search history.

(56) References Cited

U.S. PATENT DOCUMENTS

| 4,105,519 A | 8/1978 | Pennewiss et al. |
| 4,111,922 A | 9/1978 | Beede et al. |
| 4,117,184 A | 9/1978 | Erickson et al. |
| 4,272,620 A | 6/1981 | Ichimura |
| 4,612,336 A | 9/1986 | Yada et al. |
| 4,818,325 A | 4/1989 | Hiraiwa et al. |
| 4,874,822 A | 10/1989 | Rasmussen et al. |
| 4,876,126 A | 10/1989 | Takemura et al. |
| 5,005,287 A * | 4/1991 | Ritter ................. 30/41 |
| 5,008,301 A | 4/1991 | Dennis et al. |
| 5,077,352 A | 12/1991 | Elton |
| 5,084,315 A * | 1/1992 | Karimi et al. ............... 428/36.6 |
| 5,091,205 A | 2/1992 | Fan |
| 5,135,516 A | 8/1992 | Sahatjian et al. |
| 5,317,063 A | 5/1994 | Komatsu et al. |
| 5,670,557 A | 9/1997 | Dietz |
| 5,700,559 A | 12/1997 | Sheu et al. |
| 5,702,754 A | 12/1997 | Zhong |
| 5,756,144 A | 5/1998 | Wolff et al. |
| 5,804,318 A | 9/1998 | Pinchuk et al. |
| 5,985,990 A * | 11/1999 | Kantner et al. ............... 524/765 |
| 5,994,419 A | 11/1999 | Collette et al. |
| 6,048,620 A | 4/2000 | Zhong |
| 6,110,451 A | 8/2000 | Matz et al. |
| 6,120,904 A | 9/2000 | Hostettler et al. |
| 6,221,425 B1 * | 4/2001 | Michal et al. ............... 427/2.25 |
| 6,238,799 B1 | 5/2001 | Opolski |
| 6,310,116 B1 | 10/2001 | Yasuda et al. |
| 6,565,981 B1 | 5/2003 | Messner et al. |
| 6,589,665 B2 | 7/2003 | Chabrecek et al. |
| 6,673,053 B2 | 1/2004 | Wang et al. |
| 6,709,706 B2 | 3/2004 | Zhong et al. |
| 6,720,130 B1 | 4/2004 | Zhong et al. |
| 6,835,783 B1 | 12/2004 | Gartner et al. |
| 6,849,685 B2 | 2/2005 | Soerens et al. |
| 6,887,961 B2 | 5/2005 | Soerens et al. |

(Continued)

FOREIGN PATENT DOCUMENTS

EP    0 289 996    11/1988
EP    0 405 464    1/1991

(Continued)

OTHER PUBLICATIONS

International Search Report dated Aug. 8, 2007.
Written Opinion of the International Searching Authority dated Aug. 8, 2007.
Alt, V. et al., "Plasma Polymer Coating with High-Porosity Silver for Antimicrobial Protection of Osteosynthetic Devices", Osteosynthese International 2005—Kongress, Oral Presentation, No. 075, Sep. 15, 2005, 1 page.
Asha, S. K. et al., "Synthesis and Curing Studies of PPG Based Telechelic Urethane Methacrylic Macromonomers", European Polymer Journal, vol. 41, No. 1, Jan. 2005, pp. 23-33.
Guggenbichler, J.P. et al., "A New Technology of Microdispersed Silver in Polyurethane Induces Antimicrobial Activity in Central Venous Catheters", Infection, vol. 27, Suppl. 1, pp. S16-S23, 1999.

(Continued)

*Primary Examiner* — Melissa Rioja
(74) *Attorney, Agent, or Firm* — Nixon & Vanderhye P.C.

(57) ABSTRACT

The invention relates to a hydrophilic coating formulation which when cured results in a hydrophilic coating, wherein the hydrophilic coating formulation comprises a polyelectrolyte and a non-ionic hydrophilic polymer. The invention further relates to a coating system, a hydrophilic coating, a lubricious coating, use of a polyelectrolyte and a non-ionic hydrophilic polymer in a lubricious coating, an article, a medical device or component and a method of forming on a substrate a hydrophilic coating.

20 Claims, No Drawings

(56) References Cited

U.S. PATENT DOCUMENTS

| | | | |
|---|---|---|---|
| 7,264,859 B2 | 9/2007 | Rouns et al. | |
| 7,544,381 B2 | 6/2009 | Kangas | |
| 7,772,393 B2* | 8/2010 | Guire et al. | 544/196 |
| 2001/0011165 A1 | 8/2001 | Engelson et al. | |
| 2001/0027299 A1 | 10/2001 | Yang et al. | |
| 2002/0002353 A1 | 1/2002 | Michal et al. | |
| 2002/0013549 A1 | 1/2002 | Zhong et al. | |
| 2002/0018898 A1* | 2/2002 | Opolski | 428/423.1 |
| 2003/0013615 A1 | 1/2003 | Levy | |
| 2003/0096131 A1* | 5/2003 | Beavers et al. | 428/522 |
| 2004/0019168 A1 | 1/2004 | Soerens et al. | |
| 2004/0029748 A1* | 2/2004 | Levy | 508/469 |
| 2004/0043688 A1 | 3/2004 | Soerens et al. | |
| 2004/0110861 A1 | 6/2004 | Shorbu et al. | |
| 2004/0135967 A1 | 7/2004 | Carney et al. | |
| 2004/0143180 A1 | 7/2004 | Zhong et al. | |
| 2005/0054774 A1 | 3/2005 | Kangas | |
| 2005/0080157 A1 | 4/2005 | Wagener et al. | |
| 2005/0100580 A1 | 5/2005 | Osborne et al. | |
| 2005/0170071 A1 | 8/2005 | Eramo | |
| 2005/0191430 A1 | 9/2005 | Rubner et al. | |
| 2006/0240060 A1 | 10/2006 | Bavaro | |
| 2007/0167735 A1 | 7/2007 | Zhong et al. | |
| 2008/0292776 A1 | 11/2008 | Dias et al. | |
| 2008/0306455 A1 | 12/2008 | Dias et al. | |
| 2009/0169715 A1* | 7/2009 | Dias et al. | 427/2.25 |
| 2010/0113871 A1* | 5/2010 | Dias et al. | 600/101 |
| 2010/0198168 A1* | 8/2010 | Rooijmans | 604/265 |
| 2011/0046255 A1* | 2/2011 | Rooijmans | 522/11 |
| 2011/0059874 A1* | 3/2011 | Rooijmans et al. | 508/100 |

FOREIGN PATENT DOCUMENTS

| | | |
|---|---|---|
| EP | 0 480 809 | 4/1992 |
| EP | 1 065 738 | 1/2001 |
| EP | 1 621 217 | 2/2006 |
| EP | 1 776 968 | 4/2007 |
| JP | 54-147696 | 11/1979 |
| JP | 04-144567 | 5/1992 |
| JP | 5-300940 | 11/1993 |
| JP | 06-039347 | 2/1994 |
| JP | 10-211273 | 8/1998 |
| JP | 10-277144 | 10/1998 |
| JP | 10-228534 | 6/1999 |
| JP | 11-172149 | 6/1999 |
| JP | 2000-45197 | 2/2000 |
| JP | 2001-000531 | 1/2001 |
| JP | 2001-0000531 | 1/2001 |
| JP | 2007-23130 | 2/2007 |
| WO | 93/11751 | 6/1993 |
| WO | 96/28762 | 9/1996 |
| WO | WO 97/17378 | 5/1997 |
| WO | 97/29160 | 8/1997 |
| WO | 98/50461 | 11/1998 |
| WO | 98/58989 | 12/1998 |
| WO | WO 99/38546 | 8/1999 |
| WO | 01/07714 | 2/2001 |
| WO | WO 01/51103 | 7/2001 |
| WO | WO 01/92584 | 12/2001 |
| WO | 2004/056909 | 7/2004 |
| WO | WO 2004/060427 | 7/2004 |
| WO | 2004/091685 | 10/2004 |
| WO | 2006/042514 | 4/2006 |
| WO | 2006/056482 | 6/2006 |
| WO | 2007/065722 | 6/2007 |
| WO | WO 2008/012325 | 1/2008 |
| WO | 2008/031596 | 3/2008 |
| WO | WO 2008/071796 | 6/2008 |
| WO | 2008/104573 | 8/2008 |
| WO | WO 2011/157805 | 12/2011 |

OTHER PUBLICATIONS

Samuel, U. et al., "Prevention of Catheter-Related Infections: the Potential of a New Nano-Silver Impregnated Catheter", International Journal of Antimicrobial Agents, vol. 23, Suppl. 1, pp. S75-S78, Mar. 2004.

Database WPI Week 199517, *Thomas Scientific*, XP002451204 & JP 07 053895, Feb. 28, 1995 Abstract.

International Search Report for PCT/EP2006/011904 mailed Mar. 16, 2007.

Written Opinion of the International Searching Authority for PCT/EP2006/011904 mailed Mar. 16, 2007.

International Search Report for PCT/EP2007/007995 mailed Feb. 27, 2008.

Written Opinion of the International Searching Authority for PCT/EP2007/007995 mailed Feb. 27, 2008.

International Search Report for PCT/EP2008/052396 mailed Feb. 16, 2009.

Written Opinion for PCT/EP2008/052396 mailed Feb. 16, 2009.

International Search Report for PCT/EP2008/052397 mailed Jan. 13, 2009.

International Search Report for PCT/EP2009/052918 mailed Jun. 22, 2009.

Written Opinion of the International Searching Authority for PCT/EP2009/052918 mailed Jun. 22, 2009.

Japanese Patent Office, Notice of Reasons for Rejection, P2008-543747, Dispatch No. 004257 (Jan. 10, 2012) (English Translation).

Japanese Patent Office, Final Rejection, P2008-543747, Dispatch No. 472881 (Jul. 17, 2012) (English Translation).

International Search Report for PCT/EP2006/011902, dated Aug. 6, 2007.

Written Opinion of the International Searching Authority for PCT/EP2006/011902, dated Aug. 6, 2007.

International Search Report for PCT/EP2007/007984, dated Apr. 11, 2008.

Written Opinion of the International Search Authority for PCT/EP2007/007984, dated Apr. 11, 2008.

International Search Report for PCT/EP2011/060066, mailed Sep. 5, 2011.

Witten Opinion of the International Searching Authority, for PCT/EP2011/060066, mailed Sep. 5, 2011.

JP Office Action with English-Language Translation mailed Dec. 18, 2012, (Appln No. P2009-551200).

JP Office Action with English-Language Translation mailed Dec. 18, 2013, (Appln No. P2009-551201).

* cited by examiner

HYDROPHILIC COATING

This application is the U.S. national phase of International Application No. PCT/EP2006/011903 filed 11 Dec. 2006 which designated the U.S. and claims priority to European Application Nos. 05111906.3 filed 9 Dec. 2005, 06011433.7 filed 1 Jun. 2006 and 06019147.5 filed 13 Sep. 2006, the entire contents of each of which are hereby incorporated by reference.

This invention relates to a hydrophilic coating formulation which when cured results in a hydrophilic coating. The invention further relates to a coating system, a hydrophilic coating, a lubricious coating, use of a polyelectrolyte and a non-ionic hydrophilic polymer in a lubricious coating, an article, a medical device or component and a method of forming a hydrophilic coating on a substrate.

Many medical devices, such as urinary and cardiovascular catheters, syringes, and membranes need to have a lubricant applied to the outer and/or inner surface to facilitate insertion into and removal from the body and/or to facilitate drainage of fluids from the body. Lubricious properties are also required so as to minimize soft tissue damage upon insertion or removal. Especially, for lubrication purposes, such medical devices may have a hydrophilic surface coating or layer which becomes lubricious and attains low-friction properties upon wetting, i.e. applying a wetting fluid for a certain time period prior to insertion of the device into the body of a patient. A hydrophilic surface coating or layer which becomes lubricious after wetting is hereinafter referred to as a hydrophilic coating. A coating obtained after wetting is hereinafter referred to as a lubricious coating.

A well-recognized problem encountered when using lubricious coatings has been that the coatings may lose water and dry out prior to insertion into the body, or in the body when it comes in contact with e.g. a mucous membrane, such as when a urinary catheter is inserted into the urethra. Naturally, this affects the lubricity and low-friction properties of the lubricious coating, and may lead to pain and injuries of the patient when the device is inserted into the body or removed from the body.

It would therefore be advantageous to have medical devices comprising a hydrophilic coating that stays lubricious upon applying a wetting fluid for a prolonged period prior to and after insertion into the body of a patient. The time that the hydrophilic coating stays lubricious upon applying a wetting fluid is herein further referred to as dry-out time.

It is an object of the present invention to provide a hydrophilic coating that stays lubricious for a long time upon applying a wetting fluid before and after insertion into the body of a patient.

Surprisingly it has now been found that a lubricious coating with a prolonged and thereby improved dry-out time may be obtained when a polyelectrolyte and a non-ionic hydrophilic polymer are included in the hydrophilic coating from which said lubricious coating is formed by applying a wetting fluid.

It has further been found that the water uptake rate is increased in a coating of the invention comprising a polyelectrolyte in combination with a non-ionic hydrophilic polymer, compared to a similar coating without these components. This is in particular advantageous in case the article is stored with a dried coating and the coating is to be wetted prior to use. Satisfactory wetting of a coating, for instance of a catheter, may thus be accomplished within a few seconds after submersion in water or exposure to air with a relative humidity of 100%.

Within the context of the invention "lubricious" is defined as having a slippery surface. A coating on the outer or inner surface of a medical device, such as a catheter, is considered lubricious if (when wetted) it can be inserted into the intended body part without leading to injuries and/or causing unacceptable levels of discomfort to the subject. In particular, a coating is considered lubricious if it has a friction as measured on a Harland FTS5000 Friction Tester (HFT) of 20 g or less, preferably of 15 g or less, at a clamp-force of 300 g, a pull speed of 1 cm/s, a temperature of 22° C. and 35% relative humidity. The protocol is as indicated in the Examples.

The term "wetted" is generally known in the art and—in a broad sense—means "containing water". In particular the term is used herein to describe a coating that contains sufficient water to be lubricious. In terms of the water concentration, usually a wetted coating contains at least 10 wt % of water, based on the dry weight of the coating, preferably at least 50 wt %, based on the dry weight of the coating, more preferably at least 100 wt % based on the dry weight of the coating. For instance, in a particular embodiment of the invention a water uptake of about 300-500 wt % water is feasible. Examples of wetting fluids are treated or untreated water, water-containing mixtures with for example organic solvents or aqueous solutions comprising for example salts, proteins or polysaccharides. In particular a wetting fluid can be a body fluid.

An important property of such lubricious coating is that they remain lubricious as long as needed. Therefore, the dry-out time should be sufficiently long to allow application in medical devices. Within the context of the experiment, the dry-out time is the duration of the coating remaining lubricious after a device comprising the lubricious coating has been taken out of the wetting fluid wherein it has been stored and/or wetted. Dry-out time can be determined by measuring the friction in gram as a function of time the catheter had been exposed to air on the HFT (see above). The dry-out time is the point in time wherein the friction reaches a value of 20 g or higher, or in a stricter test 15 g or higher as measured at a temperature of 22° C. and 35% relative humidity.

Within the context of the invention the term polymer is used for a molecule comprising two or more repeating units. In particular it may be composed of two or more monomers which may be the same or different. As used herein, the term includes oligomers and prepolymers. Usually polymers have a number average weight (Mn) of about 500 g/mol or more, in particular of about 1000 g/mol or more, although the Mn may be lower in case the polymer is composed of relatively small monomeric units. Herein and hereinafter the Mn is defined as the Mn as determined by light scattering.

Within the context of the invention a polyelectrolyte is understood to be a high molecular weight linear, branched or crosslinked polymer composed of macromolecules comprising constitutional units, in which between 5 and 100% of the constitutional units contain ionized groups when the polyelectrolyte is in the lubricious coating. Herein a constitutional unit is understood to be for example a repeating unit, for example a monomer. A polyelectrolyte herein may refer to one type of polyelectrolyte composed of one type of macromolecules, but it may also refer to two or more different types of polyelectrolytes composed of different types of macromolecules.

Considerations when selecting a suitable polyelectrolyte are its solubility and viscosity in aqueous media, its molecular weight, its charge density, its affinity with the supporting network of the coating and its biocompatibility. Herein biocompatibility means biological compatibility by not producing a toxic, injurious or immunological response in living mammalian tissue.

For a decreased migrateability, the polyelectrolyte is preferably a polymer having a weight average molecular weight of at least about 1000 g/mol, as determinable by light scattering, optionally in combination with size exclusion chromatography. A relatively high molecular weight polyelectrolyte is preferred for increasing the dry-out time and/or reduced migration out of the coating. The weight average molecular weight of the polyelectrolyte is preferably at least 20,000 g/mol, more preferably at least 100,000 g/mol, even more preferably at least about 150,000 g/mol, in particular about 200,000 g/mol or more. For ease of applying the coating it is preferred that the average weight is 1000,000 g/mol or less, in particular 500,000 g/mol or less, more in particular 300,000 g/mol or less.

Examples of ionized groups that may be present in the polyelectrolyte are ammonium groups, phosphonium groups, sulfonium groups, carboxylate groups, sulfate groups, sulfinic groups, sulfonic groups, phosphate groups, and phosphonic groups. Such groups are very effective in binding water. In one embodiment of the invention the polyelectrolyte also comprises metal ions. Metal ions, when dissolved in water, are complexed with water molecules to form aqua ions $[M(H_2O)_x]^{n+}$, wherein x is the coordination number and n the charge of the metal ion, and are therefore particularly effective in binding water. Metal ions that may be present in the polyelectrolyte are for example alkali metal ions, such as $Na^+$, $Li^+$, or $K^+$, or alkaline earth metal ions, such as $Ca^{2+}$ and $Mg^{2+}$. In particular when the polyelectrolyte comprises quaternary amine salts, for example quaternary ammonium groups, anions may be present. Such anions can for example be halogenides, such as $Cl^-$, $Br^-$, $I^-$ and $F^-$, and also sulphates, nitrates, carbonates and phosphates.

Suitable polyelectrolytes are for example salts of homo- and co-polymers of acrylic acid, salts of homo- and co-polymers of methacrylic acid, salts of homo- and co-polymers of maleic acid, salts of homo- and co-polymers of fumaric acid, salts of homo- and co-polymers of monomers comprising sulfonic acid groups, homo- and co-polymers of monomers comprising quarternary ammonium salts and mixtures and/or derivatives thereof. Examples of suitable polyelectrolytes are poly(acrylamide-co-acrylic acid) salts, for example poly(acrylamide-co-acrylic acid) sodium salt, poly(acrylamide-co-methacrylic acid) salts, for example poly(acrylamide-co-methacrylic acid) sodium salt, poly(methacrylamide-co-acrylic acid) salts, for example poly(methacrylamide-co-acrylic acid) sodium salt, poly(methacrylamide-co-methacrylic acid) salts, for example poly(methacrylamide-co-methacrylic acid) sodium salt poly(acrylic acid) salts, for example poly(acrylic acid) sodium salt, poly(methacrylic acid) salts, for example poly(methacrylic acid) sodium salt, poly(acrylic acid-co-maleic acid) salts, for example poly(acrylic acid-co-maleic acid) sodium salt, poly(methacrylic acid-co-maleic acid) salts, for example poly(methacrylic acid-co-maleic acid) sodium salt, poly(acrylamide-co-maleic acid) salts, for example poly(acrylamide-co-maleic acid) sodium salt, poly(methacrylamide-co-maleic acid) salts, for example poly(methacrylamide-co-maleic acid) sodium salt, poly(acrylamido-2-methyl-1-propanesulfonic acid) salts, poly(4-styrene sulfonic acid) salts, poly(acrylamide-co-dialkyl ammonium chloride), quaternized poly[bis-(2-chloroethyl)ether-alt-1,3-bis[3-(dimethylamino)propyl]urea], polyallylammonium phosphate, poly(diallyldimethylammonium chloride), poly(sodium trimethyleneoxyethylene sulfonate), poly(dimethyldodecyl(2-acrylamidoethyl) ammonium bromide), poly(2-N methylpyridiniumethylene iodine), polyvinylsulfonic acids, and salts of poly(vinyl)pyridines, polyethyleneimines, and polylysines.

Particularly suitable polyelectrolytes for use in the current invention are copolymeric polyelectrolytes, wherein said copolymeric polyelectrolyte is a copolymer comprising at least two different types of constitutional units, wherein at least one type of constitutional units comprises ionizable or ionized groups and at least one type of constitutional units is absent of ionizable or ionized groups.

Ionizable is understood to be ionizable in neutral aqueous solutions, i.e. solutions having a pH between 6 and 8.

Said copolymeric polyelectrolyte may be a random or block copolymer. Generally, between 5 and 99 wt %, preferably between 50 and 90 wt %, more preferably between 70 and 85 wt % of the constitutional units comprise ionizable or ionized groups. In the lubricious coating, i.e. after wetting the hydrophilic coating, said ionizable groups may be ionized or non-ionized. Typically between 1 and 100 wt % of the total amount of ionizable and ionized groups is ionized when the copolymeric polyelectrolyte is in the lubricious coating, preferably between 30 and 100 wt %, more preferably between 50 and 100 wt %, in particular between 60 and 100 wt %.

Examples of constitutional units comprising ionizable groups are constitutional units comprising carboxylic acid groups, for example acrylic acid, methacrylic acid, maleic acid, and formic acid; sulfonic acid groups; sulfinic acid groups; and phosphonic acid groups. Examples of constitutional units comprising ionized groups are constitutional units comprising salts of the above mentioned ionizable groups, i.e. carboxylate groups, sulfonium groups, sulphinic groups, sulfate groups, phosphate groups, phosphonic groups, and phosphonium groups, and quaternary ammonium salts.

Examples of constitutional units that do not comprise ionizable groups are acrylamide, methacrylamide, vinylalcohol, methylacrylate, methylmethacrylate, vinylpyrrolidone, and vinylcaprolactam.

Examples of said copolymeric polyelectrolytes are poly(acrylamide-co-acrylic acid) salts, poly(acrylamide-co-methacrylic acid) salts, poly(methacrylamide-co-acrylic acid) salts, poly(methacrylamide-co-methacrylic acid) salts, poly(acrylamide-co-maleic acid) salts, poly(methacrylamide-co-maleic acid) salts, and poly(acrylamide-co-dialkyl ammonium chloride). Poly(acrylamide-co-acrylic acid) salts, for example the sodium salt, has been found particularly suitable for obtaining a high lubricity and dry-out time.

The use of copolymeric polyelectrolytes comprising both constitutional units comprising ionizable or ionized groups and constitutional units absent of ionizable or ionized groups has several advantages. Usually such polyelectrolytes feature a higher solubility a particular solvents and less tendency to crystallize when used in the cured hydrophilic coating.

A non-ionic hydrophilic polymer is understood to be a high molecular weight linear, branched or crosslinked polymer composed of macromolecules comprising constitutional units, in which less than 5, preferably less than 2% of the constitutional units contain ionized groups when the non-ionic hydrophilic polymer is in the lubricious coating. The non-ionic hydrophilic polymer is capable of providing hydrophilicity to a coating and may be synthetic or bio-derived and can be blends or copolymers of both. The non-ionic hydrophilic polymers include but are not limited to poly(lactams), for example polyvinylpyrrollidone (PVP), polyurethanes, homo- and copolymers of acrylic and methacrylic acid, polyvinyl alcohol, polyvinylethers, maleic anhydride based copolymers, polyesters, vinylamines, polyethyleneimines, polyethyleneoxides, poly(carboxylic acids), polyamides, polyanhydrides, polyphosphazenes, cellulosics, for example methyl cellulose, carboxymethyl cellulose, hydroxymethyl cellulose, and hydroxypropylcellulose, heparin, dextran, polypeptides, for example collagens, fibrins, and elastin, polysaccharides, for example chitosan, hyaluronic acid, alginates, gelatin, and chitin, polyesters, for example polylactides, polyglycolides, and polycaprolactones, polypeptides, for example collagen, albumin, oligo peptides, polypeptides, short chain peptides, proteins, and oligonucleotides.

It has been found that adherence between the primer layer and the surface of the article and/or the primer layer and the outer layer is improved with increasing molecular weight of the functional non-ionic hydrophilic polymer. Accordingly the weight average molecular weight of the functional non-ionic hydrophilic polymer, as determinable by as determined by light scattering, optionally in combination with size exclusion chromatography, is usually at least 20,000 g/mol, in particular at least 55,000 g/mol, preferably at least 250,000 g/mol, in particular at least 360,000 g/mol, more preferably at least 500,000 g/mol, in particular at least 750,000 g/mol.

For practical reasons (ease of application and/or ease to realise uniform coating thickness) the weight average molecular weight (Mw) is usually up to 10 million, preferably up to 5 million g/mol, more preferably up to 3 million g/mol, most preferably up to 2 million g/mol, in particular up to 1.5 million g/mol, more in particular up to 1.3 million g/mol, even more in particular up to 1 million g/mol.

In particular polyvinylpyrollidone (PVP) and polyethyleneoxide (PEO) having an Mw of at least 100000 g/mol have been found to have a particular positive effect on lubricity and a low tendency to migrate out of the coating.

In particular for polyvinylpyrrolidone (PVP) and polymers of the same class, a polymer having a molecular weight corresponding to at least K15, more in particular K30, even more in particular K80 is preferred. Particular good results have been achieved with a polymer having a molecular weight corresponding to at least K90. Regarding the upper limit, a K120 or less, in particular a K100 is preferred. The K-value is the value as determinable by the Method W1307, Revision May 2001 of the Viscotek Y501 automated relative viscometer. This manual may be found at www.ispcorp.com/products/hairscin/index_3.html The invention relates to a hydrophilic coating formulation comprising a polyelectrolyte and a non-ionic hydrophilic polymer which when applied to a substrate and cured results in a hydrophilic coating. Herein a hydrophilic coating formulation refers to a liquid hydrophilic coating formulation, e.g. a solution or a dispersion comprising a liquid medium. Herein any liquid medium that allows application of the hydrophilic coating formulation on a surface would suffice. Examples of liquid media are alcohols, like methanol, ethanol, propanal, butanol or respective isomers and aqueous mixtures thereof or acetone, methylethyl ketone, tetrahydrofuran, dichloromethane, toluene, and aqueous mixtures or emulsions thereof. The hydrophilic coating formulation further comprises components which when cured are converted into the hydrophilic coating, and thus remain in the hydrophilic coating after curing. Herein curing is understood to refer to physical or chemical hardening or solidifying by any method, for example heating, cooling, drying, crystallization or curing as a result of a chemical reaction, such as radiation-curing or heat-curing. In the cured state all or part of the components in the hydrophilic coating formulation may be crosslinked forming covalent linkages between all or part of the components, for example by using UV or electron beam radiation. However, in the cured state all or part of the components may also be ionically bonded, bonded by dipole-dipole type interactions, or bonded via Van der Waals forces or hydrogen bonds.

The term "to cure" includes any way of treating the formulation such that it forms a firm or solid coating. In particular, the term includes a treatment whereby the hydrophilic polymer further polymerises, is provided with grafts such that it forms a graft polymer and/or is cross-linked, such that it forms a cross-linked polymer.

The hydrophilic coating composition according to the invention typically comprises 1-90 wt %, preferably 3-50 wt %, more preferably 5-30 wt %, in particular 10-20 wt % of polyelectrolyte based on the total weight of the dry coating.

The non-ionic hydrophilic polymer may be used in more than 1 wt % of the hydrophilic coating formulation, for example more than 10 wt %, more than 20 wt %, or more than 30 weight %, based on the total weight of the dry coating. The non-ionic hydrophilic polymer can be present in the hydrophilic coating formulation up to 95 wt %, however, more often the non-ionic hydrophilic polymer will be used up to 50, 60, 70 or 80 wt %, based on the total weight of the dry coating.

Hereinafter all percentages of components given in the application are based on the total weight of the dry coating, i.e. the hydrophilic coating formed upon curing the hydrophilic coating composition.

The invention also relates to a hydrophilic coating obtainable by applying the hydrophilic coating formulation according to the invention to a substrate and curing it. The invention further relates to a lubricious coating obtainable by applying a wetting fluid to said hydrophilic coating, and to the use of a polyelectrolyte and a non-ionic hydrophilic polymer in a lubricious coating in order to improve its dry-out time. Further the invention relates to an article, in particular a medical device or a medical device component comprising at least one hydrophilic coating according to the invention and to a method of forming on a substrate the hydrophilic coating according to the invention.

In one embodiment of the invention the hydrophilic coating comprises the polyelectrolyte and the non-ionic hydrophilic polymer. Said hydrophilic coating is formed by curing a hydrophilic coating formulation comprising the polyelectrolyte and the non-ionic hydrophilic polymer. Preferably the polyelectrolyte and the non-ionic hydrophilic polymer are covalently and/or physically bound to each other and/or entrapped to form a polymer network after curing.

In another embodiment of the invention the hydrophilic coating comprises the polyelectrolyte, the non-ionic hydrophilic polymer and a supporting network, which may be a hydrophilic supporting network, and which is formed from a supporting monomer or polymer. Herein the supporting monomer or polymer, apart from comprising a plurality of reactive moieties capable of undergoing cross-linking reactions as described below, may also contain hydrophilic functional groups. Said hydrophilic coating is formed by curing a hydrophilic coating formulation comprising the polyelectrolyte, the non-ionic hydrophilic polymer and the supporting monomer or polymer. Preferably the polyelectrolyte and/or the non-ionic hydrophilic polymer and/or the hydrophilic supporting network are covalently linked and/or physically bound to each other and/or entrapped to form a polymer network after curing.

These embodiments, wherein the polyelectrolyte and/or the non-ionic hydrophilic polymer and/or the supporting monomer or polymer are covalently and/or physically bound in the hydrophilic coating as part of a polymer network, is particularly preferred since it has the advantage that the polyelectrolyte and the non-ionic hydrophilic polymer will not leak out into the environment of the hydrophilic coating, for example when it is coated on a medical device. This is particularly useful when the medical device is inside the human or animal body.

In the hydrophilic coating formulation which is used to produce said hydrophilic coating, the weight ratio of non-ionic hydrophilic polymer to supporting monomer or polymer may for example vary between 10:90 and 90:10, such as between 25:75 and 75:25 or such as between 60:40 and 40:60.

A supporting network can be formed upon curing a supporting monomer or polymer or any combination of supporting monomers and polymers comprising a plurality of reactive moieties capable of undergoing cross-linking reactions, which may be present in the hydrophilic coating formulation. The reactive moiety of the supporting monomer or polymer may be selected from the group consisting of radically reactive groups, such as alkenes, amino, amido, sulfhydryl (SH), unsaturated esters, ethers and amides, and alkyd/dry resins. The supporting monomer or polymer may have a backbone and at least one of the above-mentioned reactive moieties. The backbone of the supporting polymer may be selected from the group consisting of polyethers, polyurethanes, polyethylenes, polypropylenes, polyvinyl chlorides, polyepoxides, polyamides, polyacrylamides, poly(meth)acrylics, polyoxazolidones, polyvinyl alcohols, polyethylene imines, polyesters like polyorthoesters and alkyd copolymers, polypeptides, or polysaccharides such as cellulose and starch or any combination of the above. In particular, a supporting monomer, polymers with unsaturated esters, amides or ethers, thiol or mercaptan groups may suitably be used in the invention.

As used herein, the term supporting monomer refers to molecules with a molecular weight of less than approximately 1000 g/mol, and the term supporting polymer is used for molecules with a molecular weight of approximately 1000 g/mol or more.

Generally the supporting monomer or polymer has a molecular weight in the range of about 500 to about 100,000 g/mol, and preferably is a polymer with a molecular weight in the range of about 1,000 to about 10,000 g/mol. Particularly good results were obtained with a supporting polymer in the range of about 1,000 to about 6,000 g/mol. The number of reactive groups per molecule of the supporting monomer or polymer is preferably in the range of about 1.2 to about 64, more preferably in the range of about 1.2 to about 16, most preferably in the range of about 1.2 to about 8.

The supporting monomer or polymer may be used in more than 0 wt % based on the total weight of the dry coating, for example more than 10%, more than 20 wt %, more than 30 wt % or more than 40 wt %. The supporting monomer or polymer can be present in the hydrophilic coating formulation up to 90 wt %, however, more often the supporting monomer or polymer will be used up to 50 or 60 wt %, based on the total weight of the dry coating.

The hydrophilic coating formulation according to the invention can for example be cured using light visible or UV, electro-beam, plasma, gamma or IR radiation, optionally in the presence of a photoiniator or thermal initiator, to form the hydrophilic coating. Examples of photoinitiators that can be used in the hydrophilic coating are free-radical photoinitiators, which are generally divided into two classes according to the process by which the initiating radicals are formed. Compounds that undergo unimolecular bond cleavage upon irradiation are termed Norrish Type I or homolytic photoinitiators. A Norrish Type II photoinitiator interacts with a second molecule, i.e. a synergist, which may be a low molecular weight compound or a polymer, in the excited state to generate radicals in a bimolecular reaction. In general, the two main reaction pathways for Norrish Type II photoinitiators are hydrogen abstraction by the excited initiator or photoinduced electron transfer. Examples of suitable free-radical photoinitiators are disclosed in WO 00/18696 and are incorporated herein by reference. Preferred are photoinitiators are water-soluble or can be adjusted to become water-soluble, also preferred photoinitiators are polymeric or polymerisable photoinitiators.

In one embodiment of the invention the polyelectrolyte is present in a wetting fluid and introduced into the hydrophilic coating when wetting the hydrophilic coating. This is particularly useful for medical devices with a hydrophilic coating which are packed in a fluid, or wherein the hydrophilic coating is wetted in a separate wetting fluid that contains the polyelectrolyte. The invention therefore also relates to coating system for preparing a lubricious coating, said coating system comprising a coating formulation comprising a non-ionic hydrophilic polymer and a wetting fluid comprising a polyelectrolyte. Moreover the invention relates to a coating system for preparing a lubricious coating, said coating system comprising a coating formulation according to the invention and a wetting fluid comprising a polyelectrolyte.

In one embodiment of the invention the hydrophilic coating formulation according to the invention further comprises at least one surfactant, which can improve the surface properties of the coating. Surfactants constitute the most important group of detergent components. Generally, these are water-soluble surface-active agents comprised of a hydrophobic portion, usually a long alkyl chain, attached to hydrophilic or water solubility enhancing functional groups. Surfactants can be categorized according to the charge present in the hydrophilic portion of the molecule (after dissociation in aqueous solution): ionic surfactants, for example anionic or cationic surfactants, and non-ionic surfactants. Examples of ionic surfactants include Sodium dodecylsulfate (SDS), Sodium cholate, Bis(2-ethylhexyl)sulfosuccinate Sodium salt, Cetyltrimethylammoniumbromide (CTAB), Lauryldimethylamine-oxide (LDAO), N-Lauroylsarcosine Sodium salt and Sodium deoxycholate (DOC). Examples of non-ionic surfactants include Alkyl Polyglucosides such as TRITON™ BG-10 Surfactant and TRITON CG-110 Surfactant, Branched Secondary Alcohol Ethoxylates such as TERGITOL™ TMN Series, Ethylene Oxide/Propylene Oxide Copolymers, such as TERGITOL L Series, and TERGITOL XD, XH, and XJ Surfactants, Nonylphenol Ethoxylates such as TERGITOL NP Series, Octylphenol Ethoxylates, such as TRITON X Series, Secondary Alcohol Ethoxylates, such as TERGITOL 15-S Series and Specialty Alkoxylates, such as TRITON CA Surfactant, TRITON N-57 Surfactant, TRITON X-207 Surfactant, Tween 80 and Tween 20.

Typically 0.001 to 1 wt % of surfactant is applied, preferably 0.05-0.5 wt %, based on the total weight of the dry coating.

In one embodiment of the invention the hydrophilic coating formulation according to the invention further comprises at least one plasticizing agent, which can enhance the flexibility of the coating, which may be preferable when the object to be coated is likely to bend during use. Said plasticizing agent may be included in the hydrophilic coating formulation in a concentration of from about 0.01 wt % to about 15 wt % based on the total weight of the dry coating, preferably from about 1 wt % to about 5.0 wt %. Suitable plasticizers are high boiling compounds, preferably with a boiling point at atmospheric pressure of >200° C., and with a tendency to remain homogeneously dissolved and/or dispersed in the coating after cure. Examples of suitable plasticizers are mono- and polyalcohols and polyethers, such as decanol, glycerol, ethylene glycol, diethylene glycol, polyethylene glycol and/or copolymers with propylene glycol and/or fatty acids.

The invention also relates to a lubricious coating having an initial lubricity as measured on a Harland FTS Friction Tester of 20 g or less.

The hydrophilic coating according to the invention can be coated on an article. The hydrophilic coating can be coated on a substrate which may be selected from a range of geometries and materials. The substrate may have a texture, such as porous, non-porous, smooth, rough, even or uneven. The substrate supports the hydrophilic coating on its surface. The hydrophilic coating can be on all areas of the substrate or on selected areas. The hydrophilic coating can be applied to a variety of physical forms, including films, sheets, rods, tubes, molded parts (regular or irregular shape), fibers, fabrics, and particulates. Suitable surfaces for use in the invention are surfaces that provide the desired properties such as porosity, hydrophobicity, hydrophilicity, colorisability, strength, flexibility, permeability, elongation abrasion resistance and tear resistance. Examples of suitable surfaces are for instance surfaces that consist of or comprise metals, plastics, ceramics, glass and/or composites. The hydrophilic coating may be applied directly to the said surfaces or may be applied to a pretreated or coated surface where the pretreatment or coating is designed to aid adhesion of the hydrophilic coating to the substrate.

In one embodiment of the invention the hydrophilic coating according to the invention is coated on a biomedical substrate. A biomedical substrate refers, in part, to the fields of medicine, and the study of living cells and systems. These fields include diagnostic, therapeutic, and experimental human medicine, veterinary medicine, and agriculture. Examples of medical fields include opthalmology, orthopedics, and prosthetics, immunology, dermatology, pharmacology, and surgery; nonlimiting examples of research fields include cell biology, microbiology, and chemistry. The term "biomedical" also relates to chemicals and compositions of chemicals, regardless of their source, that (i) mediate a biological response in vivo, (ii) are active in an in vitro assay or other model, e.g., an immunological or pharmacological assay, or (iii) can be found within a cell or organism. The term "biomedical" also refers to the separation sciences, such as those involving processes of chromatography, osmosis, reverse osmosis, and filtration. Examples of biomedical articles include research tools, industrial, and consumer applications. Biomedical articles include separation articles, implantable articles, and ophthalmic articles. Ophthalmic articles include soft and hard contact lenses, intraocular lenses, and forceps, retractors, or other surgical tools that contact the eye or surrounding tissue. A preferred biomedical article is a soft contact lens made of a silicon-containing hydrogel polymer that is highly permeable to oxygen. Separation articles include filters, osmosis and reverse osmosis membranes, and dialysis membranes, as well as bio-surfaces such as artificial skins or other membranes. Implantable articles include catheters, and segments of artificial bone, joints, or cartilage. An article may be in more than one category, for example, an artificial skin is a porous, biomedical article. Examples of cell culture articles are glass beakers, plastic petri dishes, and other implements used in tissue cell culture or cell culture processes. A preferred example of a cell culture article is a bioreactor micro-carrier, a silicone polymer matrix used in immobilized cell bioreactors, where the geometry, porosity, and density of the particulate micro-carrier may be controlled to optimize performance. Ideally, the micro-carrier is resistant to chemical or biological degradation, to high impact stress, to mechanical stress (stirring), and to repeated steam or chemical sterilization. In addition to silicone polymers, other materials may also be suitable. This invention may also be applied in the food industry, the paper printing industry, hospital supplies, diapers and other liners, and other areas where hydrophilic, wettable, or wicking articles are desired.

The medical device can be an implantable device or an extracorporeal device. The devices can be of short-term temporary use or of long-term permanent implantation. In certain embodiments, suitable devices are those that are typically used to provide for medical therapy and/or diagnostics in heart rhythm disorders, heart failure, valve disease, vascular disease, diabetes, neurological diseases and disorders, orthopedics, neurosurgery, oncology, opthalmology, and ENT surgery.

Suitable examples of medical devices include, but are not limited to, a stent, stent graft, anastomotic connector, synthetic patch, lead, electrode, needle, guide wire, catheter, sensor, surgical instrument, angioplasty balloon, wound drain, shunt, tubing, infusion sleeve, urethral insert, pellet, implant, blood oxygenator, pump, vascular graft, vascular access port, heart valve, annuloplasty ring, suture, surgical clip, surgical staple, pacemaker, implantable defibrillator, neurostimulator, orthopedic device, cerebrospinal fluid shunt, implantable drug pump, spinal cage, artificial disc, replacement device for nucleus pulposus, ear tube, intraocular lens and any tubing used in minimally invasive surgery.

Articles that are particularly suited to be used in the present invention include medical devices or components such as catheters, for example intermittent catheters, guidewires, stents, syringes, metal and plastic implants, contact lenses and medical tubing.

The hydrophilic coating formulation can be applied to the substrate by for example dip-coating. Other methods of application include spray, wash, vapor deposition, brush, roller and other methods known in the art.

The concentration of ionic or ionizable groups in the hydrophilic coating and the thickness of the hydrophilic coating according to the invention may be controlled by altering the type of polyelectrolyte, polyelectrolyte concentration in the hydrophilic coating formulation, soaking time, drawing speed, viscosity of the hydrophilic coating formulation and the number of coating steps. Typically the thickness of a hydrophilic coating on a substrate ranges from 0.1-300 μm, preferably 0.5-100 μm, more preferably 1-30 μm.

The invention further relates to a method of forming on a substrate a hydrophilic coating which has a low coefficient of friction when wetted with a water-based liquid, wherein said hydrophilic coating comprises an polyelectrolyte.

To apply the hydrophilic coating on the substrate, a primer coating may be used in order to provide a binding between the hydrophilic coating and the substrate. The primer coating is often referred to as the primary coating, base coat or tie coat. Said primer coating is a coating that facilitates adhesion of the hydrophilic coating to a given substrate, as is described in for example WO02/10059. The binding between the primer coating and the hydrophilic coating may occur due to covalent or ionic links, hydrogen bonding, physisorption or polymer entanglements. These primer coatings may be solvent based, water based (latexes or emulsions) or solvent free and may comprise linear, branched and/or crosslinked components. Typical primer coatings that could be used comprise for example polyether sulfones, polyurethanes, polyesters, including polyacrylates, as described in for example U.S. Pat. No. 6,287,285, polyamides, polyethers, polyolefins and copolymers of the mentioned polymers.

In particular, the primer coating comprises a supporting polymer network, the supporting network optionally comprising a functional hydrophilic polymer entangled in the supporting polymer network as described in WO06/056482 A1. The information with respect to the formulation of the primer coating is herewith incorporated by reference.

A primer layer as described above is in particular useful for improving adherence of a coating comprising a hydrophilic polymer such as a polylactam, in particular PVP and/or another of the above identified hydrophilic polymers, in particular on polyvinylchloride (PVC), silicone, polyamide, polyester, polyolefin, such as polyethylene, polypropylene and ethylene-propylene rubber (e.g. EPDM), or a surface having about the same or a lower hydrophilicity.

In an embodiment, the surface of the article is subjected to oxidative, photo-oxidative and/or polarizing surface treatment, for example plasma and/or corona treatment in order to improve the adherence of the coating which is to be provided. Suitable conditions are known in the art.

Application of the formulation of the invention may be done in any manner. Curing conditions can be determined, based on known curing conditions for the photo-initiator and polymer or routinely be determined.

In general, curing may be carried out at any suitable temperature depending on the substrate, as long as the mechanical properties or another property of the article are not adversely affected to an unacceptable extent.

Intensity and wavelength of the electromagnetic radiation can routinely be chosen based on the photoinitiator of choice. In particular, a suitable wavelength in the UV, visible or IR part of the spectrum may be used.

The invention will be further illustrated by the following examples.

EXAMPLES

In the following examples hydrophilic coating formulations according to the invention and comparative coating formulations have been applied to PVC tubings, as described below, and subsequently cured to form hydrophilic coatings according to the invention.

PVC Male Catheters

Uncoated PVC tubings were coated with a hydrophilic coating. The PVC tubing had a length of 23 cm, an outside diameter of 4.5 mm (14 Fr), and an inside diameter of 3 mm. The tubings were sealed on one side in order to prevent the coating formulation to reach the inside of the tubing during dipping.

Synthesis of PTGL1000(T-H)$_2$

In a dry inert atmosphere toluene diisocyanate (TDI or T, Aldrich, 95% purity, 87.1 g, 0.5 mol), Irganox 1035 (Ciba Specialty Chemicals, 0.58 g, 1 wt % relative to hydroxy ethyl acrylate (HEA or H)) and tin(II) 2-ethyl hexanoate (Sigma, 95% purity, 0.2 g, 0.5 mol) were placed in a 1 liter flask and stirred for 30 minutes. The reaction mixture was cooled to 0° C. using an ice bath. HEA (Aldrich, 96% purity, 58.1 g, 0.5 mol) was added dropwise in 30 min, after which the ice bath was removed and the mixture was allowed to warm up to room temperature. After 3 h the reaction was complete. Poly (2-methyl-1,4-butanediol)-alt-poly(tetramethyleneglycol) (PTGL, Hodogaya, $M_n$=1000 g/mol, 250 g, 0.25 mol) was added dropwise in 30 min. Subsequently the reaction mixture was heated to 60° C. and stirred for 18 h, upon which the reaction was complete as indicated by GPC (showing complete consumption of HEA), IR (displayed no NCO related bands) and NCO titration (NCO content below 0.02 wt %).

Primer Coating Formulation (Used in Examples 1-6 and Comparative Examples A-D)

| | |
|---|---|
| PTGL1000(T-H)$_2$ | 4.25% (w/w) |
| Polyvinylpyrrolidon (1.3 M, Aldrich) (PVP) | 0.75% (w/w) |
| Irgacure 2959 (Aldrich) | 0.20% (w/w) |
| Ethanol (Merck pa) | 94.8% (w/w) |

Primer Coating Formulation (Used in Example 7)

| | |
|---|---|
| PTGL 1000(T-H)$_2$ | 4.50% (w/w) |
| Polyvinylpyrrolidon (1.3 M, Aldrich) (PVP) | 0.50% (w/w) |
| Irgacure 2959 (Aldrich) | 0.20% (w/w) |
| Ethanol (Merck pa) | 94.8% (w/w) |

Example 1

Hydrophilic Coating Formulation

| | |
|---|---|
| Polyethylene glycol diacrylate (PEG4000DA) | 5% (w/w) |
| Polyethylene oxide with $M_n$ = 200,000 g/mol (PEG 200K) (Aldrich) | 3.75% (w/w) |
| Poly(acrylamide-co-acrylic acid) partial sodium salt (14.5 wt % of Na$^+$), 20 wt % acrylamide (PAcA) (Aldrich) | 1.25% (w/w) |
| Irgacure 2959 | 0.1% (w/w) |
| Tween 80 (surfactant) (Merck) | 0.01% (w/w) |
| Distilled water | 44.94% (w/w) |
| Methanol (Merck pa) | 44.95% (w/w) |

Example 2

Hydrophilic Coating Formulation

| | |
|---|---|
| PEG4000DA | 5% (w/w) |
| PEO 200K | 3.75% (w/w) |
| PAcA | 1.25% (w/w) |
| Irgacure 2959 | 0.1% (w/w) |
| Distilled water | 44.95% (w/w) |
| Methanol | 44.95% (w/w) |

Example 3

Hydrophilic Coating Formulation

| | |
|---|---|
| PVP | 5% (w/w) |
| PAcA | 1.25% (w/w) |
| Benzophenone | 0.1% (w/w) |
| Distilled water | 46.83% (w/w) |
| Methanol | 46.83% (w/w) |

Example 4

Hydrophilic Coating Formulation

| | |
|---|---|
| PEG4000DA | 5% (w/w) |
| PEO 200K | 3.75% (w/w) |

-continued

| | |
|---|---|
| Poly(acrylic acid) sodium salt (Sigma-Aldrich, average Mw 30,000) | 1.25% (w/w) |
| Irgacure 2959 | 0.1% (w/w) |
| Distilled water | 44.95% (w/w) |
| Methanol | 44.95% (w/w) |

Example 5

Hydrophilic Coating Formulation

| | |
|---|---|
| PEG4000DA | 5% (w/w) |
| PEO 200K | 3.75% (w/w) |
| Polyacrylic acid-co-maleic acid sodium salt (Sigma-Aldrich, average Mw 70,000) | 1.25% (w/w) |
| Irgacure 2959 | 0.1% (w/w) |
| Distilled water | 44.95% (w/w) |
| Methanol | 44.95% (w/w) |

Comparative Experiment A

Coating Formulation

| | |
|---|---|
| PEG4000DA | 5% (w/w) |
| PEO 200K | 5% (w/w) |
| Irgacure 2959 | 0.1% (w/w) |
| Distilled water | 44.95% (w/w) |
| Methanol | 44.95% (w/w) |

Comparative Experiment B

Coating Formulation

| | |
|---|---|
| PVP | 5% (w/w) |
| Benzophenone | 0.1% (w/w) |
| Distilled water | 47.45% (w/w) |
| Methanol | 47.45% (w/w) |

Example 6

Hydrophilic Coating Formulation

| | |
|---|---|
| PEG4000DA | 2% (w/w) |
| PVP | 1.33% (w/w) |
| PAcA | 0.67% (w/w) |
| Irgacure 2959 | 0.04% (w/w) |
| Tween 80 | 0.04% (w/w) |
| Distilled water | 47.96% (w/w) |
| Methanol | 47.96% (w/w) |

Comparative Experiment C

Hydrophilic Coating Formulation

| | |
|---|---|
| PEG4000DA | 2% (w/w) |
| PVP | 2% (w/w) |
| Irgacure 2959 | 0.04% (w/w) |
| Tween 80 | 0.04% (w/w) |
| Distilled water | 47.96% (w/w) |
| Methanol | 47.96% (w/w) |

Comparative Experiment D

Hydrophilic Coating Formulation

| | |
|---|---|
| PEG4000DA | 2% (w/w) |
| PAcA | 2% (w/w) |
| Irgacure 2959 | 0.04% (w/w) |
| Tween 80 | 0.04% (w/w) |
| Distilled water | 47.96% (w/w) |
| Methanol | 47.96% (w/w) |

Example 7

Hydrophilic Coating Formulation Comprising Glycerol

| | |
|---|---|
| PVP | 5.50 wt % |
| PAcA | 0.75 wt % |
| Benzophenon | 0.12 wt % |
| Glycerol | 0.30 wt % |
| Distilled water | 46.67 wt % |
| Methanol | 46.67 wt % |

All ingredients were commercially obtained.

The coating obtained after curing the formulation of Example 7 is found to be lubricious, to have a good dry-out time and adheres sufficiently to the PVC catheter, also after gamma sterilisation. No visible cracks are observed by the naked eye.

Synthesis of PEG4000DA 150 g (75 mmol OH) of polyethyleneglycol (PEG, Biochemika Ultra from Fluka, Ohio value 28.02 mg KOH/g, 499.5 mew/kg, $M_n$=4004 g/mol) was dissolved in 350 ml of dry toluene at 45° C. under nitrogen atmosphere. 0.2 g (0.15 wt %) of Irganox 1035 was added as a radical stabilizer. The resulting solution was distilled azeotropically overnight (50° C., 70 mbar) leading the condensed toluene over 4 Å mol sieves. For each batch of PEG the OH value was accurately determined by OH titration, which was performed according to the method described in the $4^{th}$ edition of the European Pharmacopoeia, paragraph 2.5.3, Hydroxyl Value, page 105. This made it possible to calculate the amount of acryloyl chloride to be added and to determine the degree of acrylate esterification during the reaction. 9.1 g (90 mmol) of triethylamine was added to the reaction mixture, followed by a dropwise addition of 8.15 g (90 mmol) of acryloyl chloride dissolved in 50 ml of toluene in 1 h. Triethylamine and acryloyl chloride were colorless liquids. The reaction mixture was stirred for 2 to 4 h at 45° C. under nitrogen atmosphere. During the reaction the temperature was kept at 45° C. to prevent crystallization of PEG. To determine the conversion a sample was withdrawn from the reaction mixture, dried and dissolved in deuterated chloroform. Trifluoro acetic anhydride (TFAA) was added and a $^1$H-NMR spectrum was recorded. TFAA reacts with any remaining hydroxyl groups to form a trifluoro acetic ester, which can be easily detected using $^1$H-NMR spectroscopy (the triplet signal of the methylene protons in the α-position of the trifluoro acetic acid group (g, 4.45 ppm) can be clearly distinguished from the signal of the methylene groups in the α-position of the acrylate ester (d, 4.3 ppm)). When the degree of acrylate esterification was 98% an additional 10 mmol of acryloyl chloride and triethylamine were added to the reaction mixture allowing it to react for 1 h. At a degree of acrylate esterification >98% the warm solution was filtered to remove triethylamine hydrochloride salts. Approximately 300 ml of toluene was removed under vacuum (50° C., 20 mbar). The remaining solution was kept at 45° C. in a heated dropping funnel and added dropwise to 1 liter of diethyl ether (cooled in an ice bath). The ether suspension was cooled for 1 h before the PEG diacrylate product was obtained by filtration. The product was dried overnight at room temperature under reduced air atmosphere (300 mbar). Yield: 80-90% as white crystals.

Coating and Curing Process for Examples 1-7 and Comparative Experiments A-D

The PVC tubings were first dip-coated with the primer coating formulation, and cured using a Harland PCX coater/175/24 according to the dip protocol for the primer coating in Table 2. Subsequently the hydrophilic coating formulation was applied and cured using a Harland PCX coater/175/24 according to the dip protocol for the hydrophilic coating. The Harland PCX coater/175/24 was equipped with a Harland Medical systems UVM 400 lamp. Intensity of the lamps of the Harland PCX coater/175/24 was on average 60 mW/cm$^2$ and was measured using a Solatell Sola Sensor 1 equipped with an International Light detector SED005#989, Input Optic: W#11521, filter: wbs320#27794. The IL1400A instruction manual of International Light was applied, which is available on the internet: www.intl-light.com. The UV dose was approximately 1.8 J/cm$^2$ for the primer coating and 21.6 J/cm$^2$ for the hydrophilic coating. For applied coating parameters see Table 1.

Visual inspection of the coated PVC tubings showed good wetting of the hydrophilic coating. A uniform coating was obtained.

TABLE 1

Applied coating parameters
Coating parameters selection table

| Dipping Cycle | Primer coating | Hydrophilic coating | Range |
|---|---|---|---|
| Move device carrier to position | 125 | 125 | 2 to 175 cm |
| Speed (cm/sec) | 6.5 | 6.5 | 0.2 to 6.5 cm/sec |
| Acceleration (sec) | 0.1 | 0.1 | 0.1 cm/sec/sec |
| Move device carrier down | 11.5 | 11.5 | 2 to 175 cm |
| Speed (cm/sec) | 4 | 2 | 0.2 to 6.5 cm/sec |
| Acceleration (sec) | 0.1 | 0.1 | 0.1 cm/sec/sec |
| Move device carrier down | 27.5 | 27.5 | 2 to 175 cm |
| Speed (cm/sec) | 2 | 2 | 0.2 to 6.5 cm/sec |
| Acceleration (sec) | 0.1 | 0.1 | 0.1 cm/sec/sec |

TABLE 1-continued

Applied coating parameters
Coating parameters selection table

| Dipping Cycle | Primer coating | Hydrophilic coating | Range |
|---|---|---|---|
| Time Pause | 10 | 10 | 0 to 1800 sec |
| Move device carrier up | 28.5 | 28.5 | |
| Speed (cm/sec) | 0.3 | 1.5 (0.3 in Example 6 and Comparative exp. C and D) | 0.2 to 6.5 cm/sec |
| Acceleration (sec) | 0.1 | 0.1 | 0.1 cm/sec/sec |
| Move device carrier to position | 148 | 148 | 2 to 175 cm |
| Speed (cm/sec) | 6.5 | 6.5 | 0.2 to 6.5 cm/sec |
| Acceleration (sec) | 0.1 | 0.1 | 0.1 cm/sec/sec |
| Cure Cycle Rotator On | 2 | 2 | 1 to 8 rpm |
| Time pause | 30 (15 in Example 6 and Comparative Exp. C and D) | 360 (180 in Example 6 and Comparative Exp. C and D) | 0 to 1800 sec |

Test Methods

Lubricity Test

Lubricity tests were performed on a Harland FTS5000 Friction Tester (HFT). The protocol was selected: see Table 2 for HFT settings. Friction tester pads were used from Harland Medical Systems, P/N 102692, FTS5000 Friction Tester Pads, 0.125*0.5**0.125, 60 durometer.

Subsequently the desired test description was inserted when "run test" was activated. After inserting a guidewire into the catheter, the catheter was attached in the holder. The device was adjusted down to the desired position such that the catheter was soaked in demineralized water for 1 min. After zero gauging in water the protocol was activated by pushing "start". The data were saved after finishing. The holder was removed from the force gauge and subsequently the catheter was removed from the holder.

TABLE 2

| HFT settings | |
|---|---|
| Transport movement (cm) | 10 |
| Clamp force (g) | 300 |
| Pull speed (cm/s) | 1 |
| Acceleration time (s) | 2 |
| Number of cycles | 25 |

Dry-Out Time

Dry-out time is herein defined as the duration of the coating remaining lubricious after the device has been taken out of the wetting fluid wherein it has been stored and/or wetted. Dry-out time can be determined by measuring the friction in grams as a function of time the catheter has been exposed to air on the HFT (see above). The dry-out time is the point in time wherein the friction reaches a value of 20 g or higher, or in a stricter test 15 g or higher as measured at a temperature of 22° C. and 35% relative humidity. After inserting the guidewire into the coated PVC male catheter, the catheter was attached in the holder. The catheter was soaked in demineralized water for 1 min. The holder with the catheter was put in the force gauge and the device was jogged down to the desired position and the test was started immediately according to the same settings as for the lubricity test. Measurements were performed after 1, 2, 5, 7.5, 10, 12.5 and 15 minutes. The friction tester pads were cleaned and dried after each measurement. The data were saved after finishing. The holder was removed from the force gauge and subsequently the catheter was removed from the holder.

In Table 3 the lubricity as a function of time of the lubricious coating prepared according to Examples 1-5 is given, as well as the results of Comparative Experiments A and B.

TABLE 3

Lubricity as a function of time of the lubricious coating prepared according to Examples 1-5 and Comparative Experiments A-B.

| | Dry-out time: friction (g) in air as function of time (min) | | | | | | |
|---|---|---|---|---|---|---|---|
| | 1 min | 2 min | 5 min | 7.5 min | 10 min | 12.5 min | 15 min |
| Example 1 | 7.7 | 9.3 | 9.5 | 10.5 | 12.1 | 15.6 | 20.8 |
| Example 2 | 13.0 | 15.8 | 21.6 | 26.6 | 35.7 | 61.0 | 58.6 |
| Example 3 | 11.0 | 13.8 | 15.2 | 15.6 | 16.1 | 16.9 | 18.1 |
| Example 4 | 12 | 17 | 67 | | | | |
| Example 5 | 11 | 14 | 53 | | | | |
| Comparative Exp. A | 26.1 | 31.2 | 41.8 | 68.4 | 187.1 | 238.7 | |
| Comparative Exp. B | 21.3 | 24.1 | 54.6 | 87 | 193 | | |

The Table shows that the lubricity is significantly higher (i.e. the friction is lower) for the lubricious coatings according to the invention (Examples 1-5), comprising poly(acrylamide-co-acrylic acid) partial sodium salt, poly(acrylic acid) sodium salt or poly(acrylic acid-co-maleic acid) sodium salt, than for the lubricious coatings of Comparative Experiments A and B which do not comprise a polyelectrolyte. The lubricious coating according to the invention remained lubricious for a much longer period in the dry-out test than the coatings of the comparative examples.

In Table 4 the lubricity of the lubricious coatings prepared according to Example 6 and the Comparative Experiments C and D is given.

TABLE 4

Lubricity of the lubricious coating prepared according to Example 6 and Comparative Experiments C-D.

| | Lubricity: friction (g) under water | |
|---|---|---|
| | Initial (1 cycle) | End (25 cycles) |
| Example 6 | 1.6 | 2.4 |
| Comparative Exp. C | 5.1 | 5.8 |
| Comparative Exp. D | 52 | 434 (after 4 cycles) |

The Table shows that the coatings according to Example 6 are more lubricious (i.e. lower friction values) than the coatings according to Comparative Experiment C, which involves a coating formulation comprising a non-ionic hydrophilic polymer, but no polyelectrolyte, or Example D, which involves a coating formulation comprising a polyelectrolyte, but no non-ionic hydrophilic polymer.

The results of the lubricity measurements as a function of time (Table 3) and the lubricity measurements show that the combination of a polyelectrolyte and a non-ionic hydrophilic polymer results in a high lubricity and a high dry-out time of the coating.

The invention claimed is:

1. A hydrophilic coating formulation which when cured results in a hydrophilic coating, wherein the hydrophilic coating formulation comprises, based on the total dry weight of the hydrophilic coating formulation:
    5-30 wt. % of a polyelectrolyte selected from the group consisting of poly(acrylamide-co-acrylic acid) salts, a poly(methacrylamide-co-acrylic acid) salts, a poly (acrylamide-co-methacrylic acid) salts, poly(methacrylamide-co-methacrylic acid) salts, a poly(acrylamide-co-maleic acid) salts, poly(methacrylamide-co-maleic acid) salts, poly(acrylamide-co-dialkylammoniumchloride) and poly(methacrylamide-co-dialkylammoniumchloride),
    at least 30 wt. % of a non-ionic hydrophilic polymer,
    a free-radical photoinitiator, and
    a plasticizer in an amount of from about 0.01 wt. % to about 15 wt. %.

2. The hydrophilic coating formulation according to claim 1, wherein the non-ionic hydrophilic polymer is selected from the group consisting of poly(lactams), polyurethanes, homo- and copolymers of acrylic and methacrylic acid, polyvinyl alcohol, polyvinylethers, maleic anhydride based copolymers, polyesters, vinylamines, polyethyleneimines, polyethyleneoxides, poly(carboxylic acids), polyamides, polyanhydrides, polyphosphazenes, cellulosics, heparin, dextran, polypeptides, and polysacharrides.

3. The hydrophilic coating formulation according to claim 1, the hydrophilic coating formulation further comprising a supporting monomer and/or polymer, which comprises a plurality of reactive moieties capable of undergoing cross-linking reactions.

4. The hydrophilic coating formulation according to claim 3, wherein the supporting monomer and/or polymer is a hydrophilic supporting monomer and/or polymer.

5. The hydrophilic coating formulation according to claim 1, the hydrophilic coating formulation further comprising at least one surfactant.

6. A hydrophilic coating obtained by curing the coating formulation according to claim 1.

7. A lubricious coating obtained by applying a wetting fluid to the hydrophilic coating according to claim 6.

8. The lubricious coating according to claim 7 having an initial lubricity after 1 cycle as measured on a Harland FTS Friction Tester of 20 g or less.

9. A coating system for preparing a lubricious coating, said coating system comprising the hydrophilic coating formulation according to claim 1 and a wetting fluid comprising a polyelectrolyte.

10. An article comprising at least one hydrophilic coating according to claim 6.

11. An article according to claim 10, wherein the article is a medical device or component.

12. An article according to claim 11, wherein the medical device or component comprises a catheter, a medical tubing, a guidewire, a stent, or a membrane.

13. A method of forming on a substrate a hydrophilic coating, the method comprising applying a hydrophilic coating formulation according to claim 1 to at least one surface of the article; and allowing the coating formulation to cure by exposing the formulation to electromagnetic radiation thereby activating the free-radical photoinitiator.

14. An article comprising at least one lubricious coating according to claim 11 or 13.

15. The hydrophilic coating formulation according to claim 1, wherein the plasticizer is present in an amount of from about 1 wt. % to about 5 wt. %.

16. The hydrophilic coating formulation according to claim 1, wherein the plasticizer has a boiling point at atmospheric pressure of greater than 200° C.

17. The hydrophilic coating formulation according to claim 1, wherein the plasticizer is selected from the group consisting of mono-alcohols, polyalcohols and polyethers.

18. The hydrophilic coating formulation according to claim 1, wherein the plasticizer is selected from the group consisting of decanol, glycerol, ethylene glycol, diethylene glycol, polyethylene glycol, copolymers with propylene glycol, and fatty acids.

19. A hydrophilic coating obtained by curing the hydrophilic coating formulation according to claim 18.

20. An article comprising the hydrophilic coating according to claim 19, wherein the article is a medical device or component.

* * * * *